United States Patent [19]
Yokota et al.

[11] Patent Number: 5,807,255
[45] Date of Patent: Sep. 15, 1998

[54] POSITIONING DEVICE FOR PRODUCING CONTROLLED MOVEMENT OF THE CERVICAL SPINE

[75] Inventors: Chuckson M. Yokota, Fremont; David T. H. Hung, Palo Alto; Harrie J. M. Wolters, Menlo Park, all of Calif.

[73] Assignee: Resonex Development, Ltd., Fremont, Calif.

[21] Appl. No.: 963,554

[22] Filed: Nov. 3, 1997

Related U.S. Application Data

[63] Continuation of Ser. No. 361,791, Dec. 21, 1994, abandoned.

[51] Int. Cl.$^6$ .................................................. A61B 5/055
[52] U.S. Cl. .................................. 600/415; 5/601; 5/622
[58] Field of Search .............................. 5/601, 610, 612, 5/617, 620–624, 636; 600/415, 594, 595

[56] References Cited

U.S. PATENT DOCUMENTS

| | | | |
|---|---|---|---|
| 5,154,178 | 10/1992 | Shah | 128/653.5 |
| 5,349,956 | 9/1994 | Bonutti | 128/653.5 |

*Primary Examiner*—Ruth S. Smith
*Attorney, Agent, or Firm*—Flehr, Hohbach, Test, Albritton & Herbert

[57] ABSTRACT

A positioning device produces controlled dynamic or kinematic movement in the cervical spine of a human patient either in the flexion or extension mode while the C-spine is being examined in a magnetic resonance imaging (MRI) apparatus. For dynamic movement the head is pivotally mounted in a headrest. For kinematic movement the various images which are taken in each incremental position are combined so that a cinematic video tape is produced. No movement of the head of the patient is forced but rather by the use of a ratchet wheel, a pair of pawls, overtravel cam, and suitable external operator activating controls, the patient may freely flex his head and then lower it to the next up or flex position or alternatively, freely lower his head to the next extension or down position.

3 Claims, 11 Drawing Sheets

POSITIONING DEVICE FOR PRODUCING CONTROLLED MOVEMENT OF THE CERVICAL SPINE

This is a continuation of application Ser. No. 08/361,791 filed Dec. 21, 1994 now abandoned.

The present invention is directed to a positioning device for producing controlled movement in the cervical spine, and more specifically, where such C-spine is being examined in a magnetic resonance imaging (MRI) apparatus and where a cinematic video tape may be produced.

BACKGROUND OF THE INVENTION

Kinematic MRI imaging of various parts of the human body such as the knee and shoulder have been done before as, for example, disclosed in pending patent application Ser. No. 979,532, filed Nov. 23, 1992, entitled KINEMATIC DEVICE FOR PRODUCING PRECISE INCREMENTAL MOVEMENT IN THE KNEE. In such system a cinematic video tape can be produced as described in the above application. At the same time, the angle of such repeatable movement can be sensed by an angle encoder (transparent or invisible to the MRI signals) such as that disclosed in pending patent application Ser. No. 157,389, filed Nov. 23, 1993, entitled AUTOMATIC ANGLE ENCODER SYSTEM FOR MRI APPARATUS. In the case of the C-spine, while it is believed that a series of MRI images have been taken, this has, at the most, been done by manual operator control of the C-spine. And this is true of dynamic movement also.

And especially in the case of the C-spine, care must be taken that the patient whose cervical spine is to be examined, is neither further injured or forced to extend his range of movement beyond what is physically comfortable and that the entire process be user friendly to the patient.

OBJECT AND SUMMARY OF THE INVENTION

It is therefore a general object of the present invention to provide an improved positioning device for producing controlled movement in the C-spine of a human patient.

In accordance with the above object there is provided a method for the repeatable flexion and extension of the cervical spine of a human patient for kinematic MRI comprising the steps of restraining the head in a headrest and allowing the headrest to be flexed or lifted freely by the patient and then lowered to a next predetermined incremental position of a plurality of such positions. From a apparatus standpoint such apparatus would include a headrest for restraining the head of a patient and then ratchet means for pivotally mounting the headrest for flexion and extension of the C-spine for movement between a plurality of the predetermined incremental positions. A ratchet wheel is affixed to and movable with the headrest and at least one pawl determines the incremental position.

For dynamic MRI imaging the apparatus includes a headrest for the head of the patient and means for pivotally mounting the headrest for rotation about a fixed axis and for flexion and extension of the C-spine.

DESCRIPTION OF PREFERRED EMBODIMENT

Figure 1:
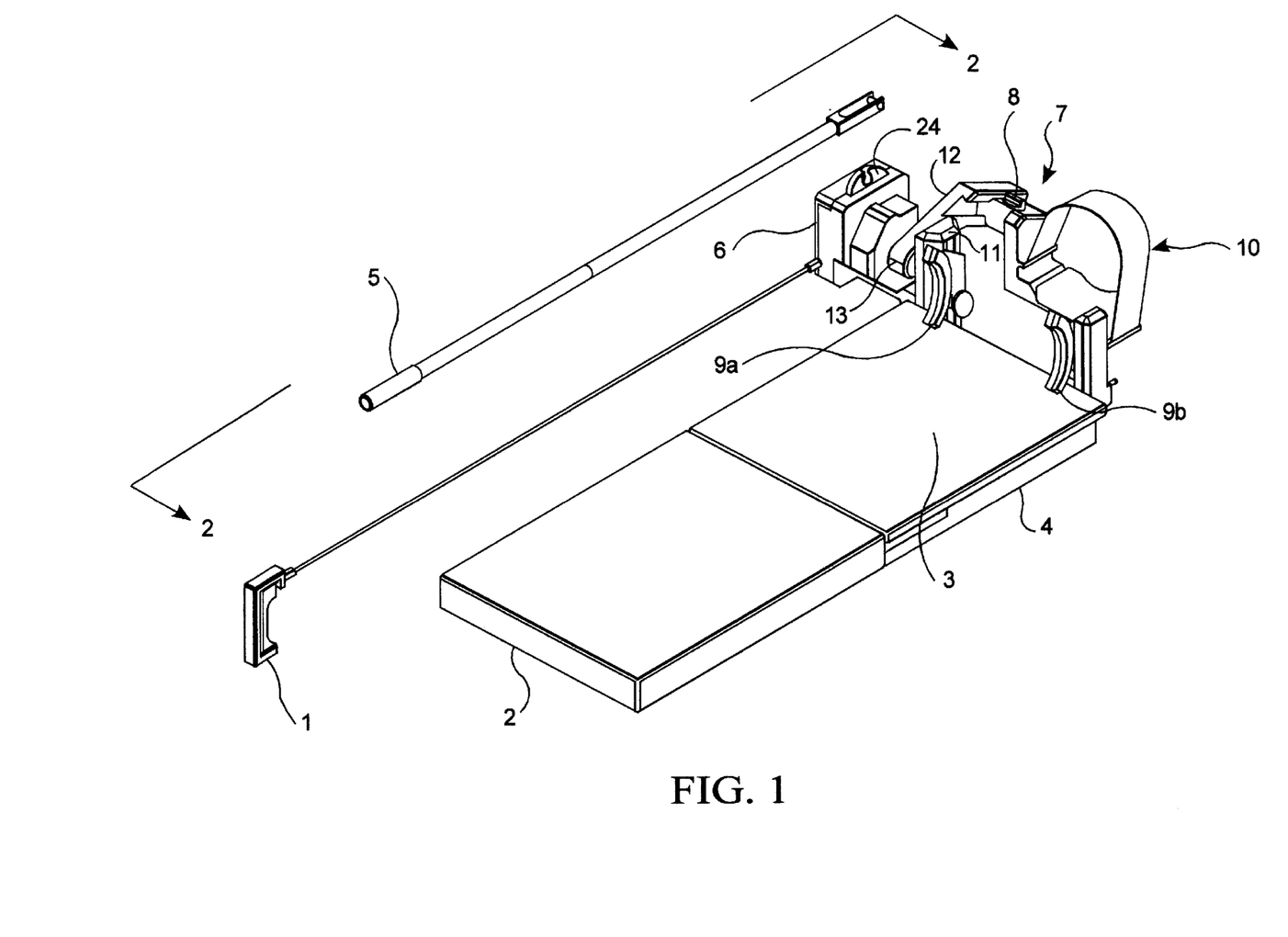
FIG. 1 is a perspective view of a positioning device embodying the present invention.

FIG. 1 shows a positioning device on which a patient is placed and then slid into the aperture or bore of an MRI device. It includes a sled pad 2 which slides into the MRI bore. The back of the patient rests on a base pad 3 and on a pair of shoulder rests 9a and 9b. A headrest 7 includes a head strap 10 for restraining the head of the patient, a clamp knob 8 for adjusting the length of an arm 12 which pivots the headrest on a pivot axis 13. Such axis extends into and is mounted for rotation within the gear box 6 which contains various components which ultimately control both the direction and kind of pivotal movement of the headrest 7.

Figure 8:
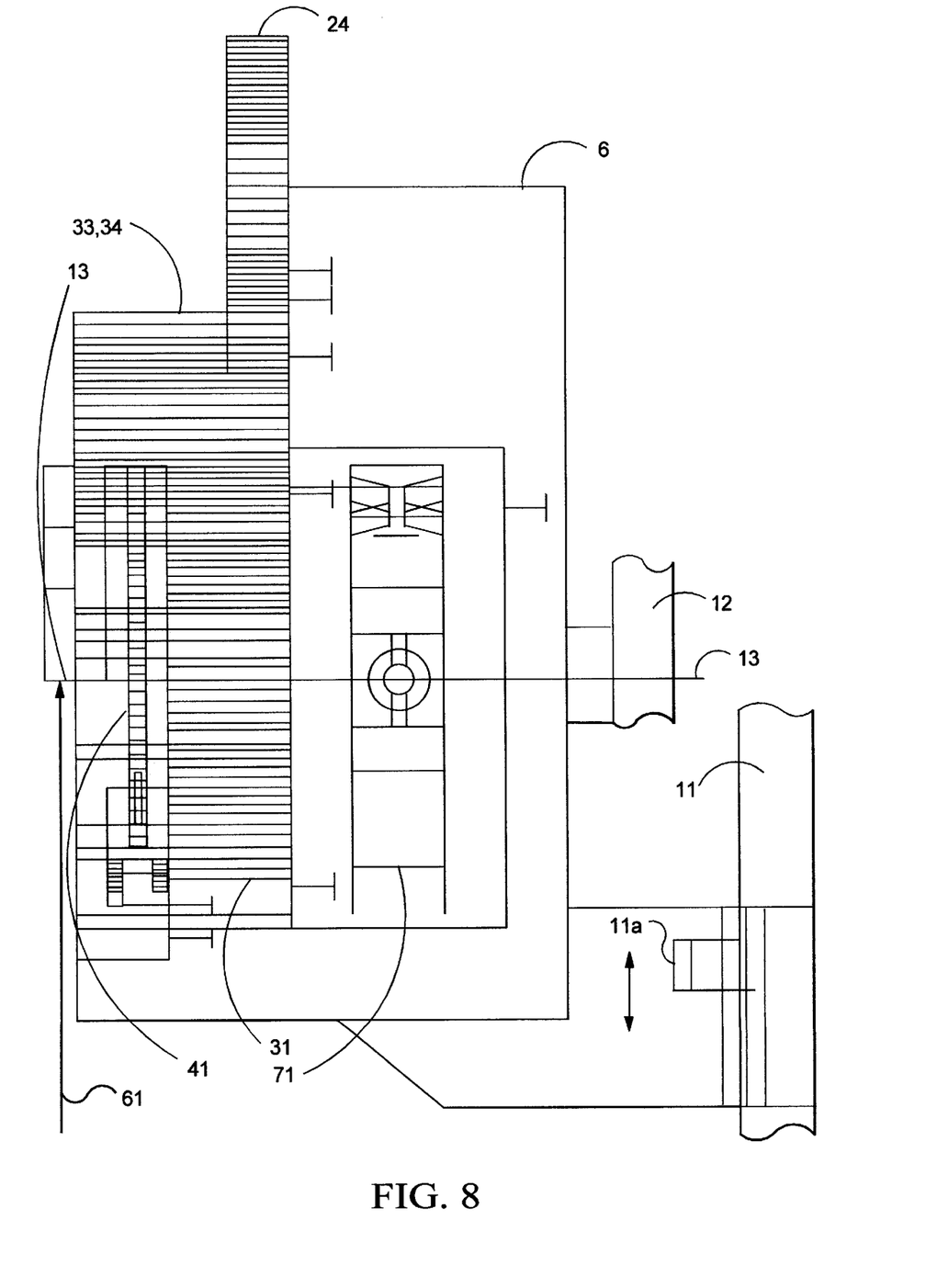
FIG. 8 is a simplified side view taken along the line 8—8 of FIG. 3.

The entire gear box 6 and headrest 7 assembly is mounted for vertical movement on post 11 on which shoulder rest 9a is also mounted. Referring briefly to FIG. 8 a knob 11a allows for adjustment as indicated by the arrows. By use of knob 11a the location of the center of rotation of the patient's neck is made to coincide with axis 13.

On gear box 6 is also mounted an elongated release rod 5 and also a flexion trigger 1.

Figure 2:
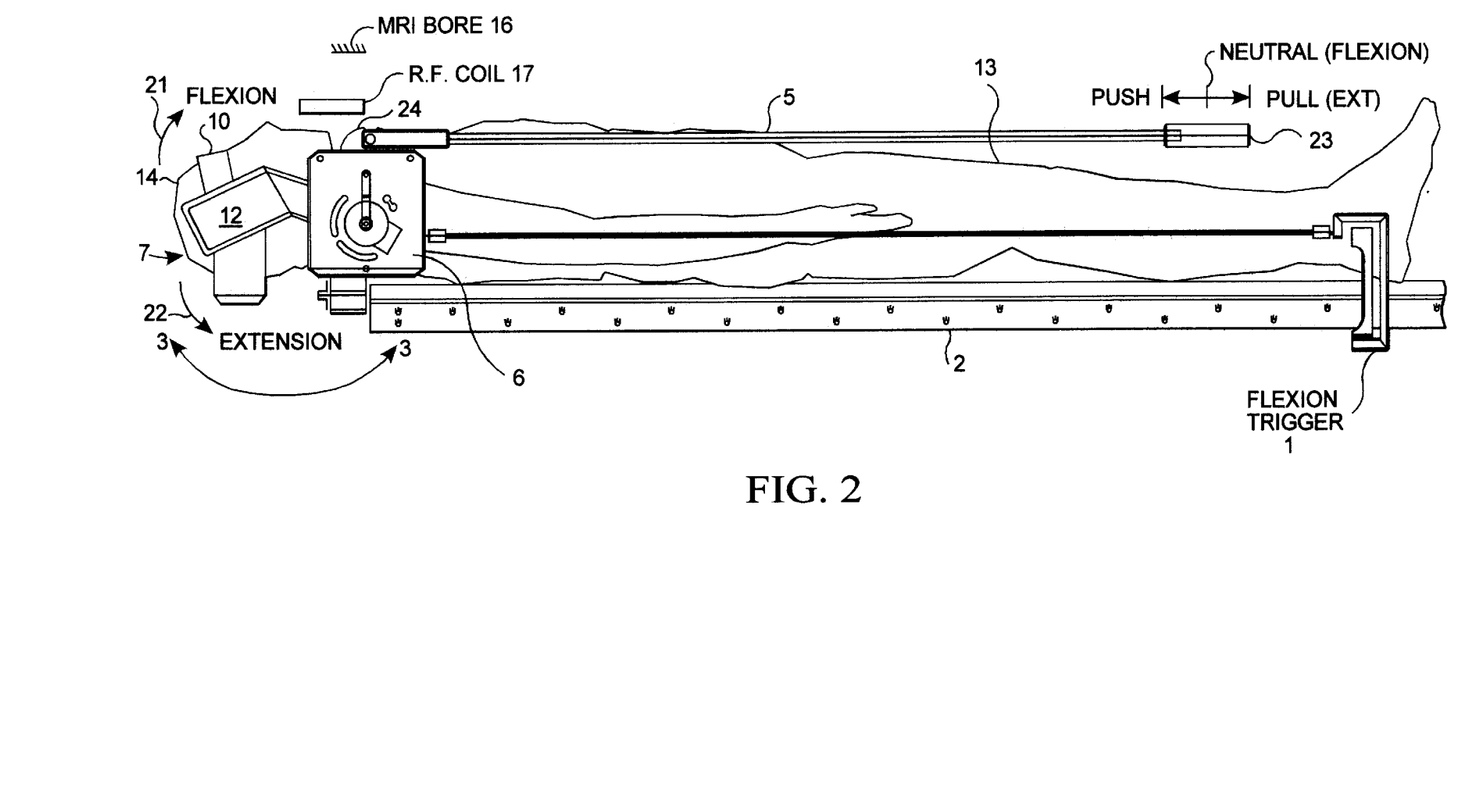
FIG. 2 is a side view taken along the line 2—2 of FIG. 1 showing a patient in the positioning device.

FIG. 2 illustrates a patient 13 reclining on the sled with the patient's head 14 in the headrest 7. The patient is illustrated as being in an MRI bore or aperture 16. An R.F. pickup coil 17 picks up the MRI imaging signals in a manner well known in the art. The coil 17 is a flexible band type coil which would be wrapped around the patient's neck. All the components shown in FIG. 2 must be transparent or invisible to the MRI signals or at least non-MRI signal producing. Thus the use of nonmagnetic materials such as plastic and polycarbonate is extensively made.

The gear box 6, as will be described below, allows the patient to freely rotate his head unit up in a flexion mode as indicated by the arrow 21 or down in an extension mode as indicated by the arrow 22. This motion is provided in repeatable 5° increments so that a series of MRI images may be taken which when linked together will provide a cinematic video tape of the motion of the C-spine either in flexion and/or extension.

From an operator control standpoint, as illustrated in FIG. 2, the operator of the MRI device in the flexion mode utilizes a flexion trigger 1 to provide for each increment of flexion motion; and in the extension mode release rod 5 is used which has the handle 23 which is movable between a push position and a pull position as illustrated. The neutral position is used when the flexion trigger is being used. Rod 5 is shown attached to the release cam 24 which is part of the gear box 6 (see also FIG. 1).

Figure 3:
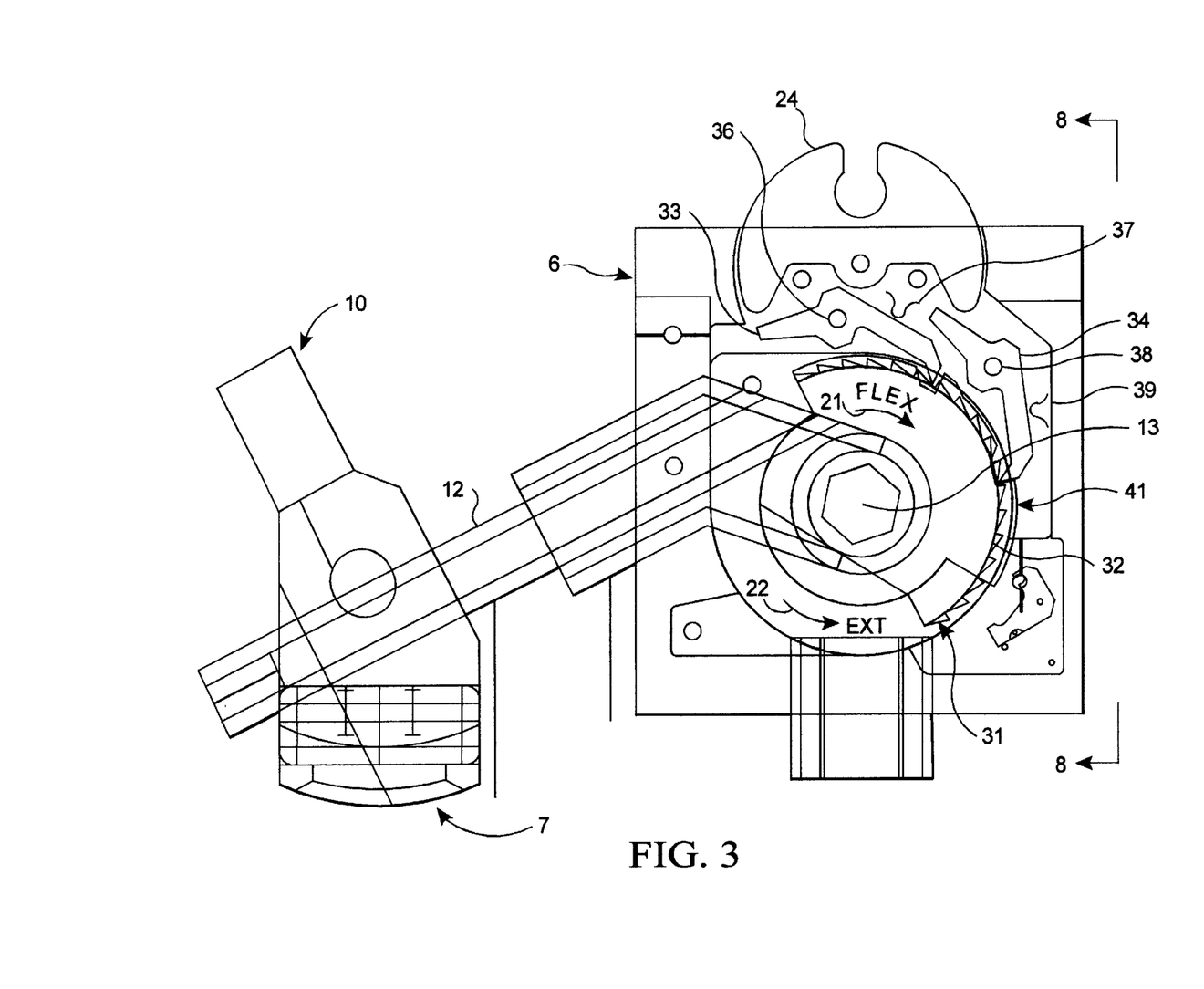
FIG. 3 is a simplified elevation or side view of a portion of FIG. 2 broken away taken along the line 3—3 of FIG. 2.

FIG. 3 illustrates the details of the gear box 6 and the headrest 7 which by arm 12 is pivoted on the common axis 13. In the gear box itself, there are several other components mounted for rotation on axis 13. The main component is a ratchet wheel or gear 31 which is fixed for rotation with the headrest 7 as shown by the arrows 21 and 22. Rotation in the clockwise direction is in the flexion mode and in a counterclockwise direction 22 in the extension mode. Ratchet wheel 31 contains a plurality of teeth 32, each of which is spaced in the preferred embodiment 5° to determine the repeatable steps of the incremental positions of the headrest 7. A pair of pawls 33 and 34 are provided which respectively alternately stop the wheel 31 successively at the incremental positions. Thus as illustrated in FIG. 3, upper pawl 33 which is pivoted at 36 and spring loaded against one of the teeth 32 by spring 37 is shown resting directly in the notch between teeth 32 to prevent any counterclockwise motion (that is, the extension motion). Pawl 34, pivoted at point 38 and biased against the teeth by spring 39 rests on the slope of a tooth 32. Rotating in the clockwise direction 21 one increment of 5° will then reverse the positions of the pawls 33 and 34. Thus one of the pawls will always be in a notch between two teeth of the ratchet gear with the other just resting on the slope of a tooth.

Thus the two pawls together define angular increments that are one half the arc of a ratchet tooth. At the same time, having a double pawl arrangement provides a fail-safe limitation of movement in an extension direction 22. If one pawl fails, then the next will limit movement to no more than two incremental positions. Such limitation of extension movement is a very desirable or necessary safety feature since for the head to accidentally fall or be extended might seriously harm the patient's C-spine. On the other hand, the ratchet arrangement allows relatively free movement in the flexion direction 21 since the spring loaded pawls will just merely ride upon the ramps or slopes of the teeth 32. This is not critical in that respect.

Figure 4:
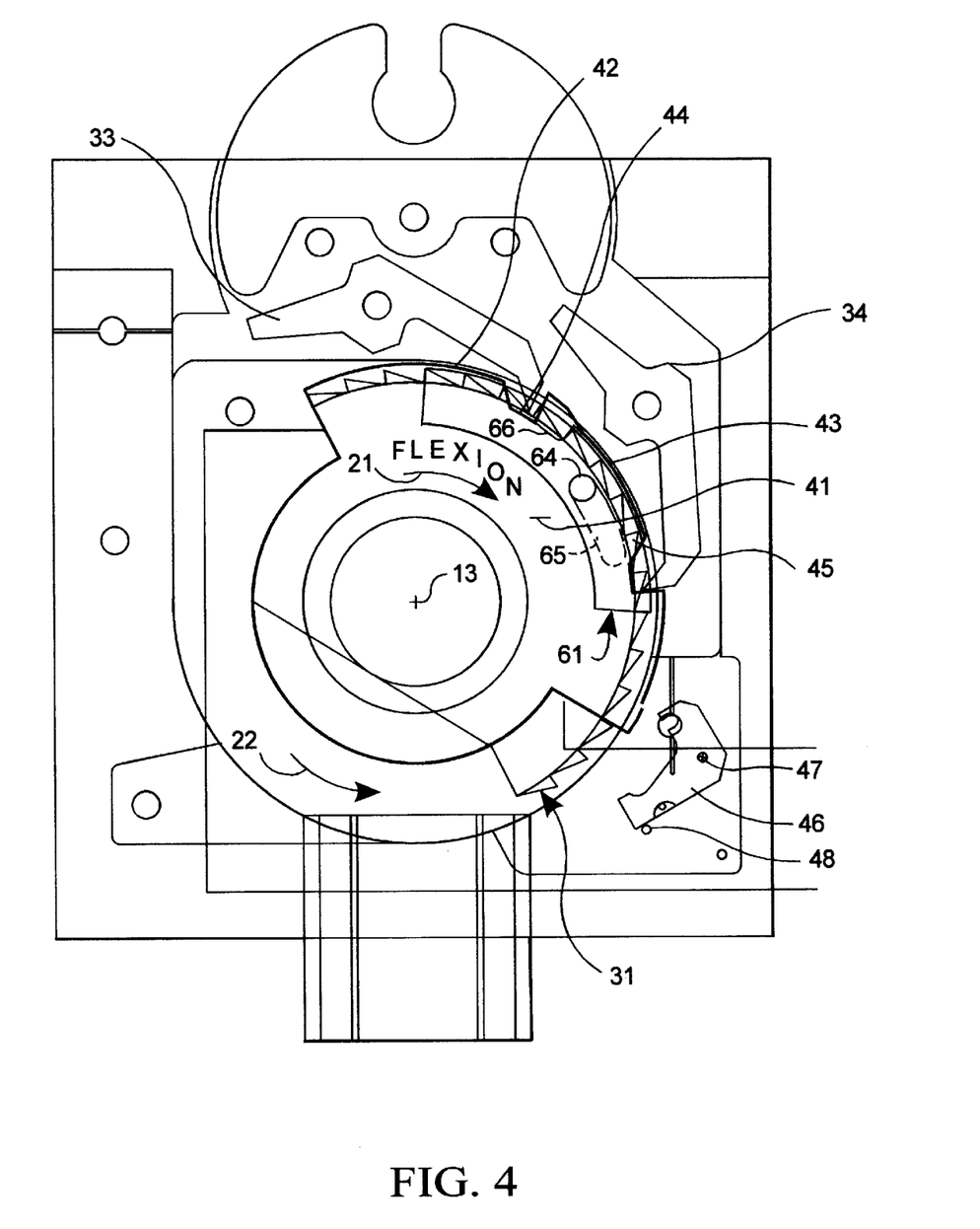
FIG. 4 is a simplified cross-section of FIG. 3 showing an over travel cam.

However, in accordance with the invention, in FIG. 4 there is provided an overtravel cam 41 mounted for rotation on the axis 13 but rather than being fixed to the ratchet wheel 31, is frictionally coupled to it by, for example, a sandwiched felt pad. Such overtravel cam 41, as shown in bold outline in FIG. 4, basically allows the patient to lift his head beyond the next angular incremental position in flexion (without the clicking or resistance of the pawls) and then when the patient lowers the head, it will position the head at the next incremental up position from the initial or last position. Thus the total relative movement is a single incremental position in the flexion direction; at the same time, the patient lifting his head in the flexion mode has free movement over several increments.

In general, the function of the overtravel cam 41 is to provide a cam surface which during movement of the ratchet wheel 31 in a flexion mode moves both pawls out of engagement so that when the patient's flexion motion is stopped, the pawls will still be on the respective shoulders 42 for the upper pawl and 43 for the lower pawl. Then when the patient lowers his head in the counterclockwise direction 22 the pawl will not intercept a tooth until it falls with one of the windows or notches 44 and 45. These notches have an effective width of substantially one tooth. Thus the overtravel cam 41 makes the flexion motion a natural and safe one for the patient.

If the overtravel function were not implemented, in order to provide incremental motion, the patient would be forced to make very short angular and jerking movements to the next position. And moreover the patient would be forced to exert a substantial torque to initiate rotation of his head and then stop only a short distance later. The overtravel mechanism allows the patient to flex easily beyond the intended position and then come back and rest (in the extension direction) in the intended position. On the other hand, the same mechanism provides that if the patient cannot flex his head from the current position into the next angular increment, then the head will naturally slip back into the current starting position. With the overtravel mechanism, the patient initiates the motion of his own head—the movement of the head is not produced from outside sources, thus removing concerns of safety and liability.

Thus FIG. 4 illustrates the first step of kinematic flexion mode where the patient lifts his head and then relaxes down. Next, because of the overtravel cam, the upper pawl 33 will fall into a notch of the ratchet gear tooth and the lower pawl 34 rests on the slope of a tooth. Thus one incremental flexion position has been done.

Figure 5:
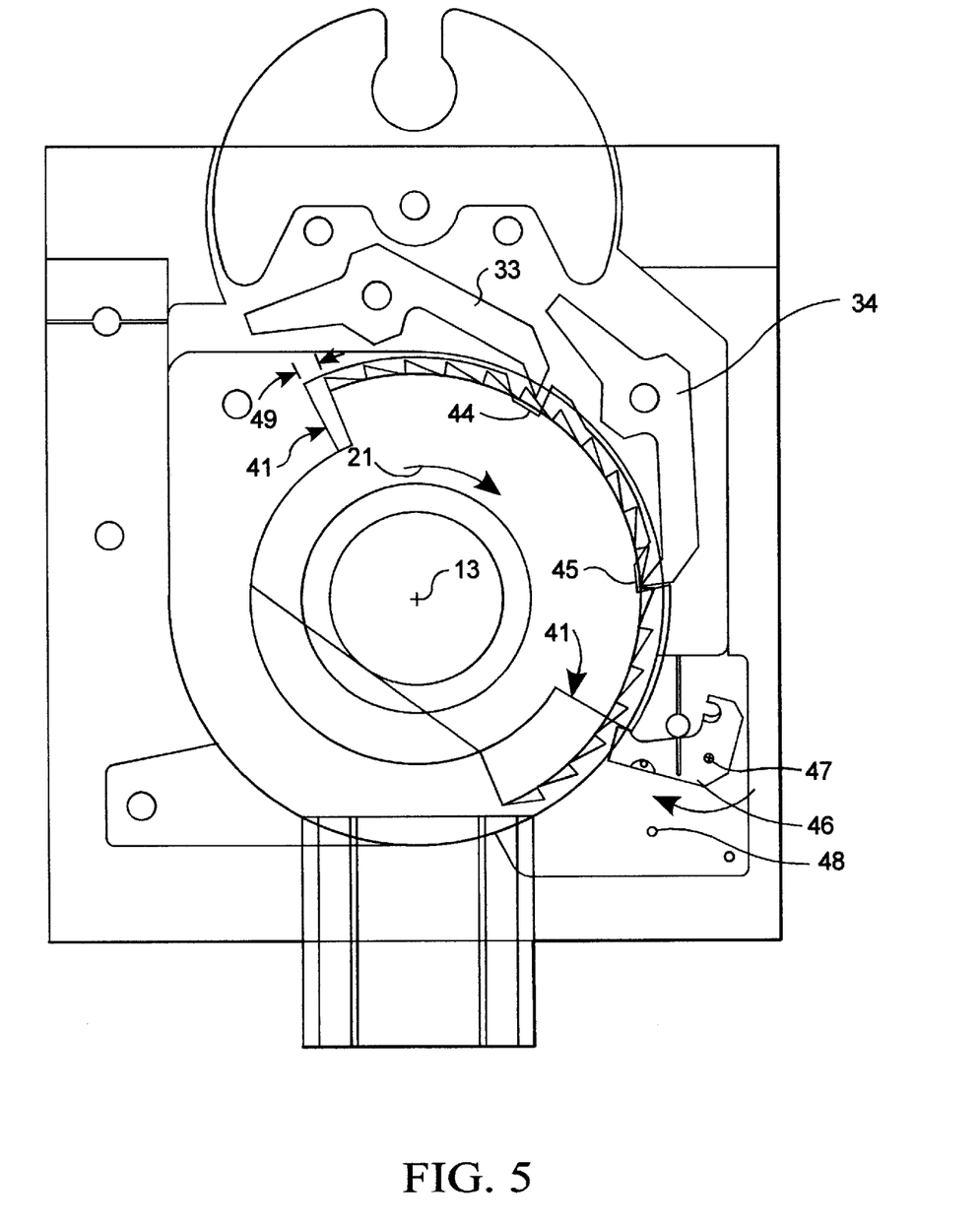
FIG. 5 is a simplified cross-section of FIG. 3 showing the operation of the over travel cam.

Then in the next sequence the flexion trigger 1 (see FIGS. 1 and 2) is activated by squeezing and releasing. This is linked to the advance lever 46 which is pivoted at 47 and normally rests on the stop 48. Movement of the flexion trigger 1 rotates the advance lever 46 as illustrated in FIG. 5 and rotates the overtravel cam 41 by the incremental distance 49. This incremental position is when the vertical edges or abutments of the notches 44 and 45 abut the pawls 33 and 34. Ratchet wheel 31 is not moved because of the frictional coupling.

Figure 6:
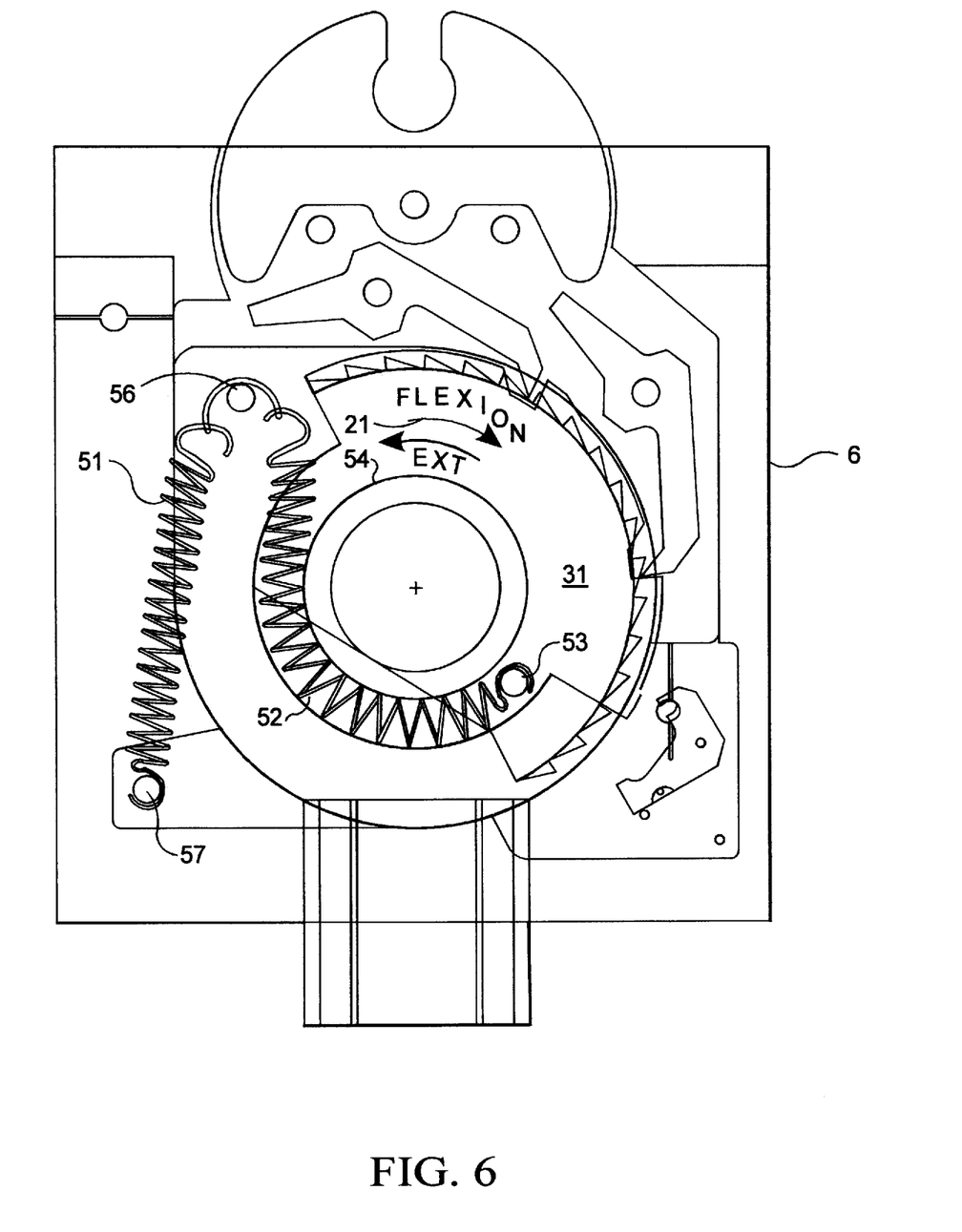
FIG. 6 is a simplified cross-section showing of FIG. 4 illustrating a spring support for the flexion mode.

Referring to FIG. 6, the flexion of the human head, especially in the horizontal position, is relatively difficult since the weight of the head must be overcome by the patient. While the patient is lying down in a supine position, the muscles that allow a person to lift or flex and extend his neck are unsuited to providing this function in the supine position. There is also concern that flexion or the extension by the patient in a supine position may cause muscle strain or other injury. Thus spring design supports motion in the flexion direction and also counterbalances the weight of the patient's head in the extension direction.

Specifically a pair of supporting springs 51 and 52 are hooked at the pin 53 on the ratchet wheel 31 to support motion in the clockwise flexion direction 21. Spring portion 52 wraps around a cylindrical surface 54 and reverses direction at a pin 56 and then is joined to the spring portion 51 and is pinned to a fixed support at 57 on the frame of the gear box 6. Thus, the comfort of the patient and avoidance of injury is promoted.

When it is desired to operate in a dynamic mode where there is free non-incremental movement in directions, as will be discussed below in connection with the dynamic release cam, it may be desirable to vary the loading on the C-spine. Of course in the flexion direction there is already the weight of the patient's head. However by adjustment of the spring force the resistance may be varied from a maximum which supports the full head weight or a minimum where the patient must overcome the weight of his head. By putting some loading on the C-spine during movement this will aid certain diagnostic techniques. And such adjustability is easily accomplished by using different size springs. Alternatively, some type of length adjustment on the spring itself may be used or still some other tensioning device.

Figure 7:
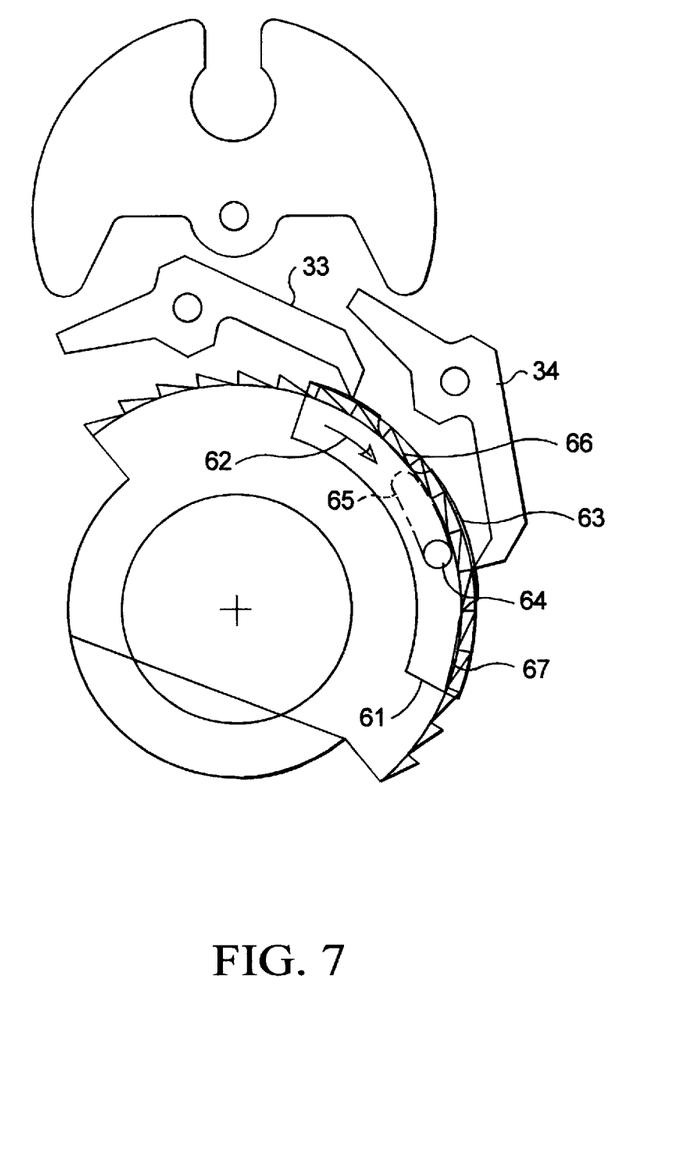
FIG. 7 is a simplified cross-section showing of FIG. 4 showing a dynamic release cam.

FIG. 7 illustrates a dynamic release cam 61 mounted on ratchet wheel 31 for rotation therewith but which has been moved in the circumferential direction shown by arrow 62 to allow a full dynamic or free non-incremental movement in either direction of the ratchet wheel 31 and its headrest 7. This is accomplished by moving the raised shoulders 63 under the pawls 33, 34, in the circumferential direction with the movement of pin 64 in the slot 65, and fixing the pin or screw 64 in that position. This will cause the upper and lower pawls 33 and 34 to be disengaged. When deactivated, cam 61 and its recesses 66, 67 allow the pawls to function normally. Referring to FIG. 4, recesses 66, 67 overlap the notches 44, 45 of overtravel cam 41. But when dynamic release cam 61 is activated its shoulders overlap the notches so that a smooth continuous shoulder is provided by the combination of overtravel and dynamic release cam. Thus free, dynamic non-incremental movement is allowed in either direction.

FIG. 8 shows in an end view the various cams and pawls in the gear box 6. In addition a fluid resistance or damper unit 71 is shown which will be described in greater detail below.

Figure 9:
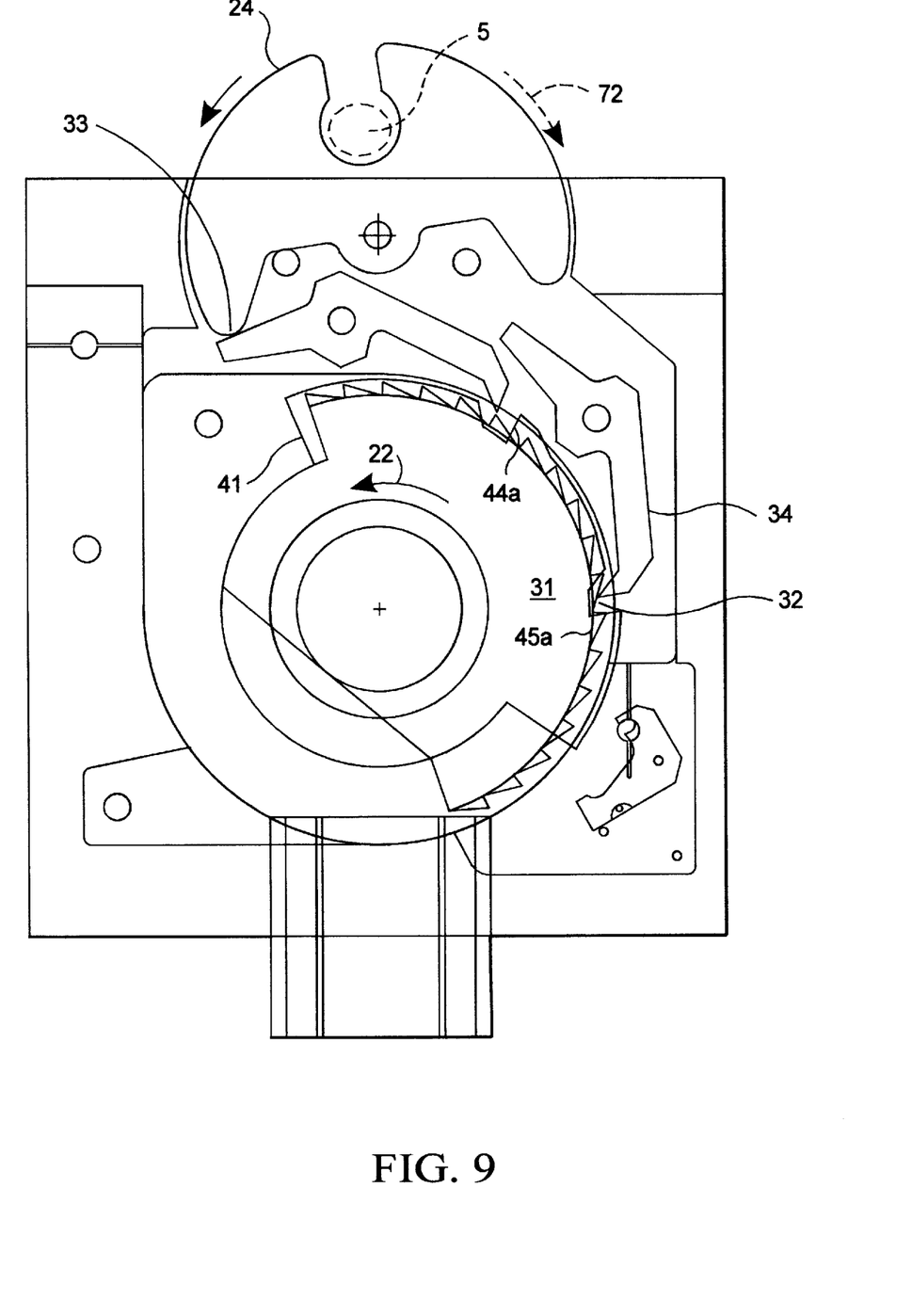
FIG. 9 is a simplified view of a portion of the FIG. 4 illustrating a step in the extension mode.

FIG. 9 illustrates the first step of an extension motion. Here, also referring to FIG. 2 the rod 5 is actuated in either a push or pull direction to move the release cam 24. In this embodiment it is assumed that it is pushed to therefore disengage the upper pawl 33. Before this is done the patient would normally be told to lift his head slightly. Then when the release rod 5 is activated, the patient lowers his head. Since the lower cam 34 is resting on a slope of the tooth 32, the ratchet gear 31 is rotated until the tooth rests against pawl 34. This is one incremental position which in the preferred embodiment is 5°.

As also illustrated in FIG. 9, the overtravel cam 41 which is useful in the flexion mode must not interfere in the extension mode. Thus when ratchet wheel 31 rotates in the direction 22 it will carry the frictionally coupled overtravel cam 41 in the same direction. However, the overtravel cam includes vertical abutments 44a and 45a on its notches 44, 45. Thus these abutments will always be intercepted by either pawl 33 or 34 to cause the overtravel cam to remain stationary even when the ratchet wheel 31 is rotated. Thus one of the two pawls 33, 34 will always rest in the next ratchet tooth. On the other hand, the overtravel cam is immediately available for functioning in the flexion mode; in other words, in an emergency, the patient can easily raise his head. Thus this is another safety feature of the present invention.

In the next step the release cam 24 is moved to its other pull position indicated by the dashed arrow 72 where pawl 34 is disengaged. Again the patient is warned to momentarily lift his head. Thus the pawls are alternately disengaged to allow the extension movement. This rocking sequence of the release cam 24 is continued until the full range of extension movement occurs.

Figure 10:
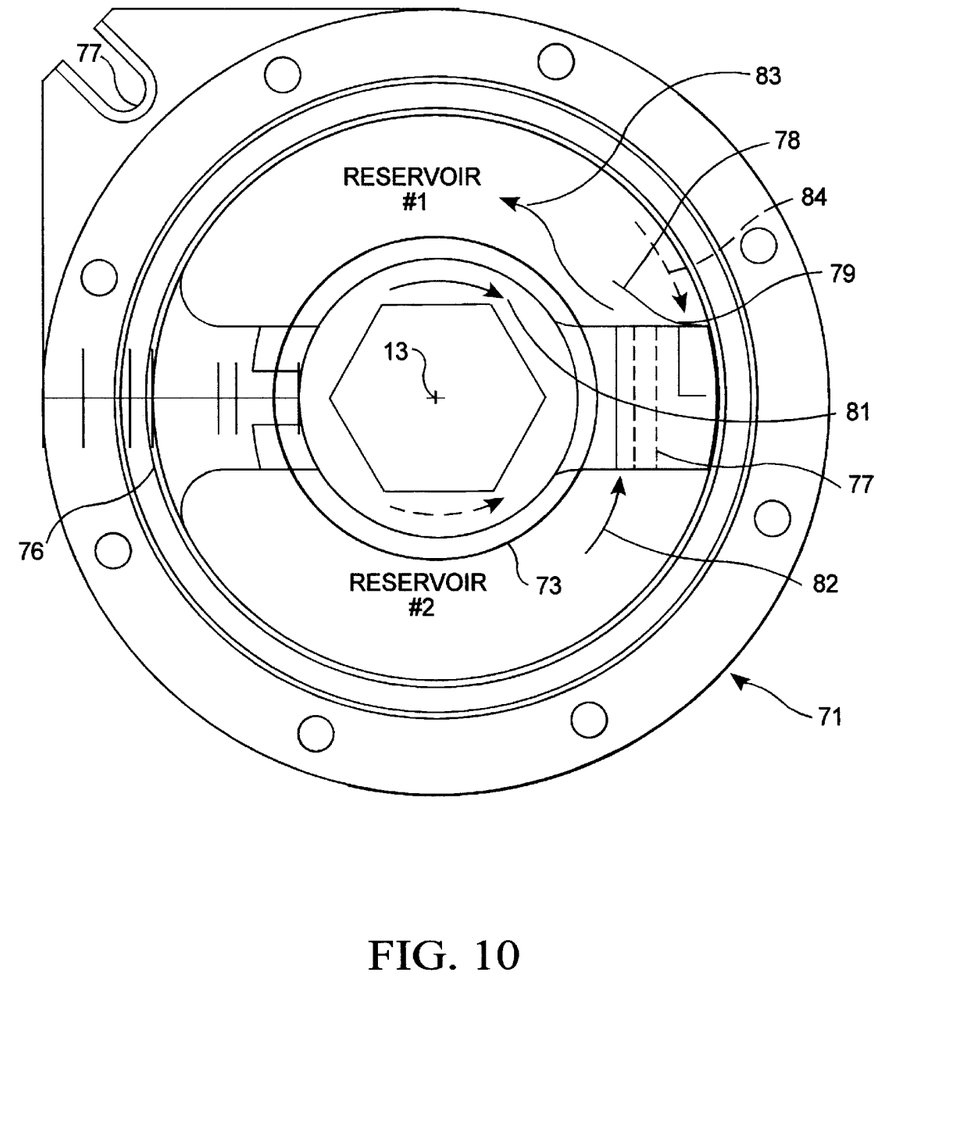
FIG. 10 is a simplified cross-sectional view of a portion of FIG. 4 and also FIG. 8.

FIG. 10 illustrates a fluid resistance or damper device 71 which has a rotatable damper vane 73 mounted for rotation on axis 13 as also illustrated in FIG. 8. Damper fluid which is transparent to MRI is in a reservoir #1 and a reservoir #2 separated by the damper vane 73. The damper vane moves relative to the damper body 76 which is affixed at the notch 77 to the remainder of the gear box 6. A through channel 77 allows communication between the two reservoirs and includes the flapper valve 78 which is hinged at 79 so that it opens during flexion rotation 81. The arrows 82 and 83 show the direction of fluid flow. Because of the relatively large passage through conduit 77, resistance to motion is relatively minimal.

In contrast in the opposite direction of rotation, the flapper valve 78 is closed and thus for movement in the extension mode in the counterclockwise direction there is relatively greater resistance. Any fluid which passes between the reservoirs is only through the crevices between the movable parts such as occur as shown by the dashed arrow 84. A typical fluid suitable for an MRI device might be a "per fluoro" type fluid sold by DuPont under the trademark FLUORINET.

Thus for kinematic use, the fluid resistance provides for easy movement in the flexion mode and greater resistance in the extension mode. For dynamic movement where free movement of the C-spine throughout its range both in extension and flexion is desired, the fluid resistance may be varied, especially with movement in extension to thereby vary the loading of the C-spine during extension. As was the case of the spring assist in flexion, such variable loading is a helpful diagnostic technique, especially in the dynamic mode. To vary this load resistance the most simple technique is to change the viscosity of the fluid. Alternatively, a variable needle valve could be inserted in the movable vane 73.

Figures 11A, 11B:
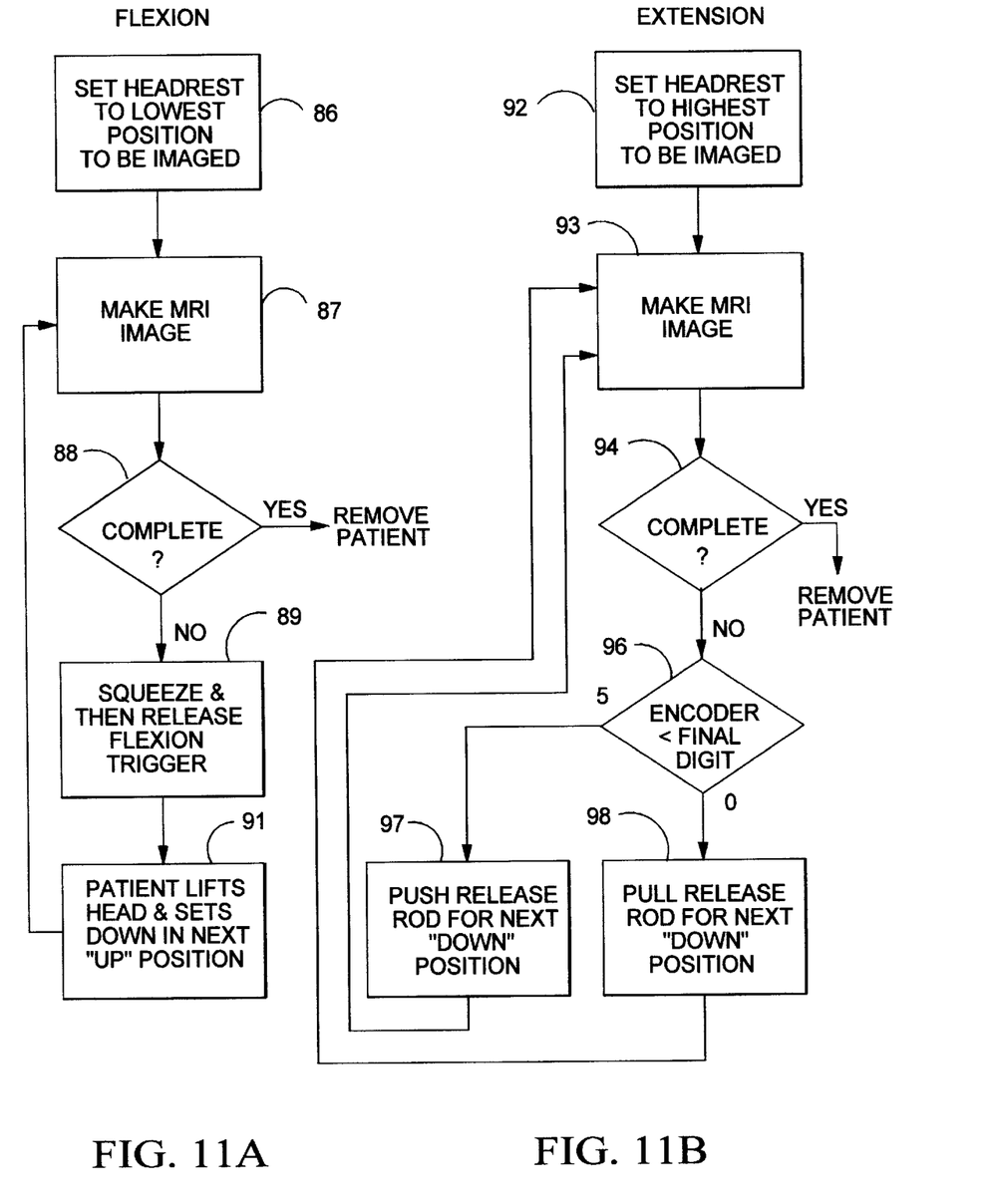
FIGS. 11A and 11B are flow charts illustrating two modes of operation of the invention.

FIGS. 11a and 11b show the general steps as discussed in detail above to make a cinematic video tape using several successive MRI images both for the flexion and extension modes. Referring to FIG. 11a, in step 86 the headrest is set to the lowest position and then in step 87 an image made. If this is the first image, in step 88 the process continues. The number of images is determined by the range of movement which, for example, depends on the physical condition of the patient. For example, this may be 50° and ten images. If another image is to be taken, the next successive incremental position is moved to, in step 89 where the flexion trigger is squeezed and released. In step 91 the patient lifts his head and sets down in the next flexion position. A return is made to step 87 for the next image.

FIG. 11b shows the extension process where in step 92 the headrest is set to the highest position to be imaged. Thereafter the first image is made in step 93 and in step 94 successive images are made by going to step 96 where here the operator of the angle encoder is told whether to push or pull the release rod. For example, a final digit may be 0 or 5 depending upon whether it is pulled or released. But this may be varied as desired. Then the steps either 97 or 98 are implemented by the operator and the patient is told to lift slightly and then relax in the next down position and the sequence is again repeated.

The present invention is equally useful in a dynamic mode where free movement of the head in extension and flexion is permitted. This is provided, of course, by the dynamic release cam. With the use of the headrest which restrains the head of the patient and the pivotal mounting about a fixed axis, the pivoted headrest immobilizes the head except for the desired movement in flexion and extension. This is an especially important in the case of MRI imaging (as compared to X-ray) where any undesired movement cannot be tolerated. Furthermore this dynamic mode of operation is enhanced by including the adjustment that makes the effective center of rotation of the C-spine (or neck) substantially coincide with the fixed pivot axis. Finally in the dynamic mode, to provide for variable loading of the C-spine, in a flexion mode the spring assist may be maximized, lowered or eliminated; and in the extension mode, the fluid resistance varied.

Thus an improved kinematic and dynamic apparatus for imaging the cervical spine has been provided.

What is claimed is:

1. Apparatus for the flexion and extension of the C-spine of a human patient for dynamic MR imaging, said C-spine having an effective center of rotation comprising a headrest including means for restraining the head of said patient during rotation of said headrest;

means for pivotally mounting said headrest for rotation about a fixed axis for said flexion and extension of said C-spine;

and adjustment means connected to said means for pivotally mounting said headrest for making said effective center of rotation of said C-spine substantially coincide with said fixed axis.

2. Apparatus as in claim 1 including fluid resistance means coupled to said headrest and said pivotal mounting means for providing resistance to movement.

3. Apparatus as in claim 2 where said fluid resistance means includes means for providing less resistance in flexion than extension.

* * * * *